US010428127B2

(12) United States Patent
Willbold et al.

(10) Patent No.: US 10,428,127 B2
(45) Date of Patent: Oct. 1, 2019

(54) CYCLIC, AMYLOID BETA-BINDING PEPTIDES AND THE USE THEREOF

(71) Applicant: FORSCHUNGSZENTRUM JUELICH GMBH, Juelich (DE)

(72) Inventors: Dieter Willbold, Juelich (DE); Oleksandr Brener, Duesseldorf (DE)

(73) Assignee: Forschungszentrum Juelich GmbH (DE)

( * ) Notice: Subject to any disclaimer, the term of this patent is extended or adjusted under 35 U.S.C. 154(b) by 96 days.

(21) Appl. No.: 15/022,712

(22) PCT Filed: Sep. 23, 2014

(86) PCT No.: PCT/DE2014/000476
§ 371 (c)(1),
(2) Date: Mar. 17, 2016

(87) PCT Pub. No.: WO2015/043566
PCT Pub. Date: Apr. 2, 2015

(65) Prior Publication Data
US 2018/0111971 A1    Apr. 26, 2018

(30) Foreign Application Priority Data
Sep. 26, 2013    (DE) .................. 10 2013 016 002

(51) Int. Cl.
| C07K 14/47 | (2006.01) |
| A61K 38/12 | (2006.01) |
| C07K 7/64 | (2006.01) |
| G01N 33/68 | (2006.01) |
| A61P 25/28 | (2006.01) |
| A61K 38/00 | (2006.01) |

(52) U.S. Cl.
CPC .......... *C07K 14/4711* (2013.01); *A61K 38/12* (2013.01); *A61P 25/28* (2018.01); *C07K 7/64* (2013.01); *G01N 33/6896* (2013.01); *A61K 38/00* (2013.01); *G01N 2333/4709* (2013.01)

(58) Field of Classification Search
None
See application file for complete search history.

(56) References Cited

U.S. PATENT DOCUMENTS

| 7,354,756 B1 | 4/2008 | Benkovic et al. |
| 2013/0156723 A1 | 6/2013 | Gonzalez |

FOREIGN PATENT DOCUMENTS

| CN | 1179040 C | 12/2004 |
| CN | 101454671 A | 6/2009 |
| CN | 104380110 A | 2/2015 |
| CN | 102224168 B | 3/2015 |
| CN | 104380111 B | 8/2017 |
| DE | 699 30 164 | 11/2006 |
| DE | 10 2005 049 537 | 4/2007 |
| DE | 10 2012 102 998 | 10/2013 |
| DE | 10 2012 102 999 | 10/2013 |
| WO | WO-00/36093 | 6/2000 |
| WO | WO-01/034631 A2 | 5/2001 |
| WO | WO-01/034631 A3 | 5/2001 |
| WO | WO-02/081505 | 10/2002 |
| WO | WO-2013/021353 | 2/2013 |

OTHER PUBLICATIONS

Dictionary.com "Destroy" accessed from dictionary.com on Feb. 1, 2018 (Year: 2018).*
Willbold "Peptide for the diagnosis and therapy of Alzheimer's disease"—a machine translation of WO/2002/081505 (Year: 2002).*
Google "Dictionary: Overall" accessed from google on Jul. 23, 2018 (Year: 2018).*
Google "Dictionary: directly" accessed from google on Jul. 24, 2018 (Year: 2018).*
Gross "Bond-order discrimination by atomic force microscopy" science 337 (Year: 2012).*
Kapurniotu Aphrodite et al: "Conformational restriction via cyclization in beta-amyloid peptide abeta(1-28) leads to an inhibitor of Abeta(1-28) amyloidogenesis and cytotoxicity.", Chemistry & Biology Feb. 2003, vol. 10, No. 2, Feb. 2003 (Feb. 2003), pp. 149-159, XP026904712, ISSN: 1074-5521 Abstract: p. 156, col. 1, paragraph 3; figures; tables.
Rahimipour S et al: "In Vitro and Mechanistic Studies of an Anti-Amyloidogenic Architechture", Biopolymers, vol. 100, No. 3, Sp. Iss. Si, May 2013 (May 2013), p. 230, XP009182097, & 23rd American Peptide Symposium: Waikoloa, HI, USA; Jun. 22-27, 2013 abstract.
Sievers Stuart A et al: "Structure-based design of non-natural amino-acid inhibitors of amyloid fibril formation", Nature, Nature Publishing Group, United Kingdom, vol. 475, No. 7354, Jul. 1, 2011 (Jul. 1, 2011), pp. 96-100, XP001526382, ISSN: 0028-0836. DOI: 10.1038/NATURE10154 p. 99, col. 1.
Demattos, R.B.; [u.a.]; Peripheral anti-A beta antibody alters CNS and plasma A-beta clearance and decreases brain A-beta burden in a mouse model of Alzheimer's disease. 2001. In: PNAS, vol. 98, S. 8850-8855.
Comparison of Biosequenees Temple F. Smith and Michael S. Waterman Advances in Applied Mathematics 2,482-489 (1981).
A General Method Applicable to the Search for Similarities in the Amino Acid Sequence of Two Proteins Saul B. Needleman and Christian D. Wunsch J. MD. Biol. (1970) 48+ 443-453.
Katsara, Maria et al.; "Round and Round We Go: Cyclic Peptides in Disease", Current Medicinal Chemistry 2006, vol. 13, No. 19; May 10, 2006; pp. 2221-2232.

* cited by examiner

*Primary Examiner* — Adam Weidner
(74) *Attorney, Agent, or Firm* — Jordan and Koda, PLLC

(57) ABSTRACT

A peptide comprising at least one peptide binding to an amyloid beta species, wherein the peptide includes an amino acid sequence that is present in cyclized form. The use of the peptides in medicine, in particular for treating Alzheimer's disease, is disclosed.

18 Claims, 5 Drawing Sheets
Specification includes a Sequence Listing.

SEQUENCE LISTING

```
<160> NUMBER OF SEQ ID NOS: 23

<210> SEQ ID NO 1
<211> LENGTH: 24
<212> TYPE: PRT
<213> ORGANISM: Artificial Sequence
<220> FEATURE:
<223> OTHER INFORMATION: D-Peptid, cRD2D3

<400> SEQUENCE: 1

Pro Thr Leu His Thr His Asn Arg Arg Arg Arg Arg Pro Arg Thr
1               5                   10                  15

Arg Leu His Thr His Arg Asn Arg
            20

<210> SEQ ID NO 2
<211> LENGTH: 24
<212> TYPE: PRT
<213> ORGANISM: Artificial Sequence
<220> FEATURE:
<223> OTHER INFORMATION: D-Peptide, cD3D3

<400> SEQUENCE: 2

Arg Pro Arg Thr Arg Leu His Thr His Arg Asn Arg Arg Pro Arg Thr
```

```
1               5                   10                  15

Arg Leu His Thr His Arg Asn Arg
            20

<210> SEQ ID NO 3
<211> LENGTH: 12
<212> TYPE: PRT
<213> ORGANISM: Artificial Sequence
<220> FEATURE:
<223> OTHER INFORMATION: D-Peptide, cRD2

<400> SEQUENCE: 3

Pro Thr Leu His Thr His Asn Arg Arg Arg Arg Arg
1               5                   10

<210> SEQ ID NO 4
<211> LENGTH: 24
<212> TYPE: PRT
<213> ORGANISM: Artificial Sequence
<220> FEATURE:
<223> OTHER INFORMATION: D-Peptide, cRD2RD2

<400> SEQUENCE: 4

Pro Thr Leu His Thr His Asn Arg Arg Arg Arg Arg Pro Thr Leu His
1               5                   10                  15

Thr His Asn Arg Arg Arg Arg Arg
            20

<210> SEQ ID NO 5
<211> LENGTH: 13
<212> TYPE: PRT
<213> ORGANISM: Artificial Sequence
<220> FEATURE:
<223> OTHER INFORMATION: D-Peptide, cD3r

<400> SEQUENCE: 5

Arg Pro Arg Thr Arg Leu His Thr His Arg Asn Arg Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: D-Peptide, cD3p

<400> SEQUENCE: 6

Arg Pro Arg Thr Arg Leu His Thr His Arg Asn Arg Pro
1               5                   10

<210> SEQ ID NO 7
<211> LENGTH: 13
<212> TYPE: PRT
<213> ORGANISM: Artificial Sequence
<220> FEATURE:
<223> OTHER INFORMATION: D-Peptide, cD3a

<400> SEQUENCE: 7

Arg Pro Arg Thr Arg Leu His Thr His Arg Asn Arg Ala
1               5                   10

<210> SEQ ID NO 8
<211> LENGTH: 12
<212> TYPE: PRT
<213> ORGANISM: Artificial Sequence
<220> FEATURE:
```

-continued

<223> OTHER INFORMATION: D-Peptide, cD3

<400> SEQUENCE: 8

Arg Pro Arg Thr Arg Leu His Thr His Arg Asn Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: D-Peptide, cDB3

<400> SEQUENCE: 9

Arg Pro Ile Thr Arg Leu Arg Thr His Gln Asn Arg
1               5                   10

<210> SEQ ID NO 10
<211> LENGTH: 24
<212> TYPE: PRT
<213> ORGANISM: Artificial Sequence
<220> FEATURE:
<223> OTHER INFORMATION: D-Peptide, cDB3DB3

<400> SEQUENCE: 10

Arg Pro Ile Thr Arg Leu Arg Thr His Gln Asn Arg Arg Pro Ile Thr
1               5                   10                  15

Arg Leu Arg Thr His Gln Asn Arg
            20

<210> SEQ ID NO 11
<211> LENGTH: 12
<212> TYPE: PRT
<213> ORGANISM: Artificial Sequence
<220> FEATURE:
<223> OTHER INFORMATION: D-Peptide, cD3(p2k)

<400> SEQUENCE: 11

Arg Lys Arg Thr Arg Leu His Thr His Arg Asn Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: D-Peptide, D3

<400> SEQUENCE: 12

Arg Pro Arg Thr Arg Leu His Thr His Arg Asn Arg
1               5                   10

<210> SEQ ID NO 13
<211> LENGTH: 12
<212> TYPE: PRT
<213> ORGANISM: Artificial Sequence
<220> FEATURE:
<223> OTHER INFORMATION: D-Peptide, prtrlhthrnrr

<400> SEQUENCE: 13

Pro Arg Thr Arg Leu His Thr His Arg Asn Arg Arg
1               5                   10

<210> SEQ ID NO 14
<211> LENGTH: 12
<212> TYPE: PRT

```
<213> ORGANISM: Artificial Sequence
<220> FEATURE:
<223> OTHER INFORMATION: D-Peptide, rtrlhthrnrrp

<400> SEQUENCE: 14

Arg Thr Arg Leu His Thr His Arg Asn Arg Arg Pro
1               5                   10

<210> SEQ ID NO 15
<211> LENGTH: 12
<212> TYPE: PRT
<213> ORGANISM: Artificial Sequence
<220> FEATURE:
<223> OTHER INFORMATION: D-Peptide, trlhthrnrrpr

<400> SEQUENCE: 15

Thr Arg Leu His Thr His Arg Asn Arg Arg Pro Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: D-Peptide, rlhthrnrrprt

<400> SEQUENCE: 16

Arg Leu His Thr His Arg Asn Arg Arg Pro Arg Thr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: D-Peptide, lhthrnrrprtr

<400> SEQUENCE: 17

Leu His Thr His Arg Asn Arg Arg Pro Arg Thr Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: D-Peptide, hthrnrrprtrl

<400> SEQUENCE: 18

His Thr His Arg Asn Arg Arg Pro Arg Thr Arg Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: D-Peptide, thrnrrprtrlh

<400> SEQUENCE: 19

Thr His Arg Asn Arg Arg Pro Arg Thr Arg Leu His
1               5                   10

<210> SEQ ID NO 20
<211> LENGTH: 12
<212> TYPE: PRT
<213> ORGANISM: Artificial Sequence
```

```
<220> FEATURE:
<223> OTHER INFORMATION: D-Peptide, hrnrrprtrlht

<400> SEQUENCE: 20

His Arg Asn Arg Arg Pro Arg Thr Arg Leu His Thr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: D-Peptide, rnrrprtrlhth

<400> SEQUENCE: 21

Arg Asn Arg Arg Pro Arg Thr Arg Leu His Thr His
1               5                   10

<210> SEQ ID NO 22
<211> LENGTH: 12
<212> TYPE: PRT
<213> ORGANISM: Artificial Sequence
<220> FEATURE:
<223> OTHER INFORMATION: D-Peptide, nrrprtrlhthr

<400> SEQUENCE: 22

Asn Arg Arg Pro Arg Thr Arg Leu His Thr His Arg
1               5                   10

<210> SEQ ID NO 23
<211> LENGTH: 12
<212> TYPE: PRT
<213> ORGANISM: Artificial Sequence
<220> FEATURE:
<223> OTHER INFORMATION: D-Peptide, rrprtrlhthrn

<400> SEQUENCE: 23

Arg Arg Pro Arg Thr Arg Leu His Thr His Arg Asn
1               5                   10
```

CYCLIC, AMYLOID BETA-BINDING PEPTIDES AND THE USE THEREOF

The invention relates to cyclic, amyloid beta-binding peptides and the use thereof.

BACKGROUND OF THE INVENTION

The intein-mediated cyclization of peptides is known from DE 699 30 164 T2.

Anti-Aß directed antibodies for treating Alzheimer's disease are known from DeMattos et al. (DeMattos, R. B., Bales, K. R., Cummins, D. J., Dodart, J.-C., Paul, S. M., Holtzman, D. M. (2001). Peripheral anti-Aß antibody alters CNS and plasma Aß clearance and decreases brain Aß burden in a mouse model of Alzheimer's disease. In: PNAS, Vol. 98, pgs. 8850-8855).

However, there is still no drug available for the treatment of Alzheimer's disease (AD, Latin Morbus Alzheimer) which acts to combat the cause. Drugs that are used are able to alleviate some symptoms at best, but cannot slow, let alone stop, the progression of the disease.

A number of substances exist that, in animal experiments, are able to achieve some successes in terms of prevention, but not necessarily in the treatment, of Alzheimer's disease.

One trait of Alzheimer's disease is extracellular deposits of the amyloid beta peptide (A beta peptide, Aß, or Aß peptide). These deposits of the A beta peptide in plaque are typically found in the brains of AD patients post mortem. This is the reason why various forms of the A beta peptide, such as fibrils, are considered to be responsible for the development and progression of the diseases. Additionally, for some years now, small, freely diffusable A beta oligomers have been regarded as the primary causative factor in the development and progression of AD. A beta monomers are continuously created in our body and are presumably not toxic per se. There is speculation as to whether A beta monomers agglomerate to form A beta oligomers randomly as a function of the concentration thereof, which ultimately results from formation and decomposition rates in the body, and thus, with increasing age, are increasingly likely to do so spontaneously. Once A beta oligomers have developed, it is possible that they multiply by way of a prion-like mechanism and ultimately lead to disease.

At present, several substances exist that reduce the concentration of A beta monomers in a wide variety of ways, for example by way of gamma secretase inhibition or modulation, A beta-binding antibodies, and so forth, which appears to suffice to provide successful preventive action in animal experiments (animals are usually already undergoing treatment before the symptoms of the disease fully manifest themselves). In clinical human studies, in phases II and III, only individuals that have been clearly diagnosed with Alzheimer's disease are allowed to be treated. This is where all these substances have failed so far. It is possible that, after the onset of the disease, a small or moderate decrease in the A beta monomer concentration is no longer sufficient to prevent the development of increasingly greater amounts of A beta oligomers.

To date, there it is not possible to diagnose Alzheimer's disease before symptoms appear. Today, Alzheimers disease is primarily detected through neuropsychological tests on persons already suffering from symptoms of dementia. Furthermore, other diseases, such as traumas, can be excluded by way of various examination methods. However, it is known that A beta oligomers, and subsequently plaque, develop in the brain of patients up to 20 years prior to the appearance of symptoms and cause irreversible damage. Molecular probes, which are intravenously injected into the patient and bind to A beta oligomers and plaque after passing the blood-brain barrier, can be rendered visible by way of imaging methods, and thus allow an early diagnosis of Alzheimer's disease.

The disadvantage of the existing A beta-binding substances is that they have insufficient affinity to prevent the multiplication of A beta oligomers.

Another disadvantage is that there are no probes for in vivo imaging methods which bind specifically to A beta species and render these visible. Since A beta oligomers play such an important and early role in the history of the disease, exactly this would be desirable.

SUMMARY OF THE INVENTION

It is the object of the invention to provide peptides for a
A) causal treatment of Alzheimer's disease by preventing the formation of toxic A beta oligomers or aggregates and/or by detoxifying the same, or a
B) reliable diagnosis of Alzheimer's disease by providing probes for in vivo imaging.

Hereafter, the terms "A beta," "amyloid beta," "amyloid ß" and "Aß" are used synonymously.

The object is achieved by the inventive peptides comprising at least one peptide binding to an amyloid beta species, wherein the peptide includes a linear amino acid sequence which enables it to bind A beta, and this property is either preserved or amplified by the peptide being present in cyclized form by way of a covalent bond, and by the kit, by the composition, by the probe, and the uses of the peptides according to the additional independent claims. Advantageous embodiments will be apparent from the respective claims dependent thereon.

Peptides according to the invention comprise at least one peptide binding to an amyloid beta species, such as the D3 known from the related art, wherein the peptide comprises a linear amino acid sequence enabling the peptide to bind to A-beta, and this property is either preserved or amplified by the linear peptide being present in cyclized form by way of a covalent bond.

The described peptide D3 is known, with the linear sequence thereof, from the publication WO 02/081505 A2.

The peptides according to the invention are advantageously substantially composed of D-enantiomeric amino acids. Within the meaning of the present invention, the expression "substantially composed of D-enantiomeric amino acids" shall mean that at least 60%, preferably 75%, 80%, particularly preferably 85%, 90%, 95%, and in particular 96%, 97%, 98%, 99% or 100% of the amino acids to be used will be D-enantiomeric amino acids.

In one embodiment of the invention, the cyclized peptide according to the invention binds amyloid beta species with a dissociation constant ($K_D$ value) of no more than 1 µM, preferably 800, 600, 400, 200, 100, 10 nm, particularly preferably 1000, 900, 800, 700, 600, 500, 400, 300, 200, 100 pM, especially preferably no more than 50 pM, and most preferably no more than 25, 20, 15, 10, 9, 8, 7, 6, 5, 4, 3, 2, 1 pM to sub-pM, wherein any intermediate value is possible.

In an advantageous embodiment of the invention, the dissociation constant ($K_D$ value) of the cyclized peptide is advantageously reduced compared to binding peptides having a linear sequence, in particular, however, preferably compared to each of the linear peptides from which the cyclized peptide can be derived. This is associated with improved properties of the peptides according to the invention, such as binding affinity and effectiveness of the decomposition and/or of the prevention of the formation of toxic amyloid beta species. This applies in particular, but not exclusively, to a low $K_D$ value at the high-affinity site of the A beta (monomer, oligomer, and fibrils).

The peptide according to the invention advantageously comprises an amino acid sequence in which the cyclization of the linear molecule has been carried out, for example, by a covalent bond of the first amino acid with the last amino acid, such as by way of a condensation reaction. Other options for cyclization exist, of course, for example by coupling other amino acids to each other. The coupling of the second amino acid to the last amino acid shall only be mentioned by way of example. Any possible other coupling is equally conceivable.

If the first and last amino acids of the peptide are coupled to each other, this advantageously results in no open ends being present in the peptide chain (amino acid sequence).

A further result of this measure is that all peptides having linear amino acid sequences that, after cyclization, yield the same, no longer distinguishable amino acid order, are identical in this regard.

Example: The linear amino acid sequence of the known peptide D3 (SEQ ID NO. 12) is rprtrlhthrnr. The corresponding cyclized peptide "cD3" (SEQ ID NO. 8) coupled between the N-terminal amino group and the C-terminal carboxyl group by way of an amide bond is no longer distinguishable from the cyclized peptides prtrlhthrnrr (SEQ ID NO. 13), rtrlhthrnrrp (SEQ ID NO. 14), trlhthrnrrpr (SEQ ID NO. 15), rlhthrnrrprt (SEQ ID NO. 16), lhthrnrrprtr (SEQ ID NO. 17), hthrnrrprtrl (SEQ ID NO. 18), thrnrrprtrlh (SEQ ID NO. 19), hrnrrprtrlht (SEQ ID NO. 20), rnrrprtrlhth (SEQ ID NO. 21), nrrprtrlhthr (SEQ ID NO. 22), or rrprtrlhthrn (SEQ ID NO. 23).

The production of cyclized peptides is state of the art and can be carried out, for example, according to the methods as described in DE 102005049537 A1.

The cyclization via the first and last amino acids of the peptide advantageously also means that there are no longer any "open" ends of the peptide chain, which often represent points of attack for peptide-decomposing activities in cells, animals or humans, such as by way of aminopeptidases and carboxypeptidases.

Cyclized peptides advantageously have greater stability in animals and humans than the corresponding linear peptides. However, this effect alone is not decisive for the present invention, as will be described hereafter. Incidentally, as was shown, this effect also applies only for the case of a head-to-tail or tail-to-head cyclization, in which the two ends of the linear peptide are correspondingly coupled to each other.

Within the scope of the invention, it was rather found that the cyclized peptides according to the invention have a higher binding affinity to A beta species, and particularly the especially toxic amyloid beta oligomers, than linear binding peptides from which the cyclized peptide can be derived. This means that the $K_D$ value is lower in the cyclized peptides than in linear peptides, and in particular lower than in linear peptides from which these can be derived.

In a further preferred embodiment of the invention, the binding affinity of the cyclized peptides according to the invention, compared to linear peptides from which they can be derived, is increased by 1%, 2, 3, 4, 5, 6, 7, 8, 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, in particular 100%, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, in particular 200%, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, in particular 300%, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, in particular 400%, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, advantageously even 500%, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, particularly advantageously 600%, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, particularly advantageously 700%, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, likewise particularly advantageously 800%, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, likewise particularly advantageously 900%, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or even by 1000%, or even by 10000%, or even by as much as 100000% or 1000000%, wherein any intermediate value is possible. This applies in particular, but not exclusively, to an increased affinity with the high-affinity site of the A beta (monomer, oligomer, fibrils and so forth).

This is indicated by a correspondingly reduced $K_D$ value. Compared to a linear, binding peptide, preferably compared to every linear binding peptide from which the cyclized peptide can be derived, the $K_D$ value, as a measure of the binding affinity of the cyclized peptide to amyloid beta species, and in particular to amyloid beta oligomers, is reduced by 1%, 2, 3, 4, 5, 6, 7, 8, 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, in particular 99.1, 99.2, 99.3, 99.4, 99.5%, 99.6, 99.7, 99.8, 99.9 to 99.99, or even 99.999%.

Advantageously, these lower $K_D$ values refer in particular, but not exclusively, to the high-affinity site of the A beta (monomer, oligomer, fibrils, and so forth).

Cyclized peptides according to the invention can therefore be used more efficiently as probes for diagnostic purposes than linear, binding peptides, in particular more efficiently than the linear peptide analogs thereof from which they can be derived (same amino acid sequence).

However, they can in particular also be used more efficiently as therapeutic agents than linear peptides, and in particular more efficiently than the linear peptide analogs thereof from which they can be derived.

The reason is that, within the scope of the invention, it was further recognized that the cyclized peptides according to the invention additionally prevent the formation of particularly toxic amyloid beta oligomers, or cause the destruction and/or detoxification thereof, with higher effectiveness or efficiency than linear peptides, in particular than the peptide analogs thereof having linear sequences from which the cyclized peptides can be derived. This effectiveness is in particular increased by 1%, 2, 3, 4, 5, 6, 7, 8, 9, in particular 10%, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74.75, 76, 77, 78, 79, 80, 81, 82, 83, 84, 85, 86, 87, 88, 89, 90, 91, 92, 93, 94, 95, 96, 97, 98, 99, 99.9, and particularly advantageously even by 100%.

For this purpose, a sample comprising different Aβ conformers is fractionated, for example, in the simplest case as an experiment. In each fraction, different conformers, such as monomers, oligomers, fibrils or higher aggregates, are enriched corresponding to the fractionating step and can then be exactly determined.

The expression "exactly determined" comprises a calibration step during the fractionating, with molecules of a known behavior. After fractionating, only a certain type of conformers of the Aβ is present in each fraction, such as monomers, oligomers or fibrils, and so forth.

For example, the conformers are separated according to the s value or sedimentation coefficient thereof in density gradient centrifugation, serving as the fractionating step. Molecules of differing sizes can have an identical hydrodynamic radius, but nonetheless have different s values and are separated according to these. Calibration using molecules having a known s value allows the Aβ conformers obtained by way of density gradient centrifugation to be exactly determined according to the s value thereof.

Thereafter, the resultant fractions are treated with and without an active ingredient and determined by way of RP-HPLC, for example. In this way, it is possible to determine the effectiveness of the active ingredient.

A further method is described hereafter. The so-called QIAD (quantitative determination of interference with Aβ aggregate size distribution) test can be used for the quantitative analysis of active ingredients. The method for quantitatively analyzing the influence of an active ingredient on the particle size distribution of amyloid peptides and/or proteins in a sample comprises the following steps. First, A beta is allowed to aggregate under controlled conditions, whereby different A beta aggregates develop. The conditions are selected so that a particularly high number of small, especially cytotoxic A beta oligomers are formed. Next, the substance to be examined, such as one of the cyclized peptides according to the invention, is added to the sample. The active ingredient changes the particle size distribution in the sample. This change is established quantitatively. The change is a measure of the reduction, or even of the complete elimination, of certain toxic species of a certain particle size. The QIAD method is used to measure the increase or the decrease in A beta aggregates having a certain particle size. While some A beta aggregates having a certain size were initially present in the sample, these are reduced, or even completely eliminated, under the influence of the active ingredient. Other particle sizes increase or remain constant under the influence of the active ingredient. The particles that are formed from the A beta are preferably separated from each other according to the hydrodynamic radius of the particles. In this way, advantageously a multitude of fractions are obtained from the sample. The particles of amyloid peptides and/or proteins having a certain aggregate size are enriched in the fractions. This separation of the particles can be carried out by way of density gradient centrifugation. The fractions are spatially separated from each other, such as by way of pipetting them off. Finally, the concentration of A beta in the respective fraction is determined by completely denaturing the A beta species during a reverse phase (RP-) HPLC carried out subsequent to the fractionating. The denaturing of the aggregates can take place completely, for example using 30% acetonitrile and 0.1% trifluoroacetic acid at a column temperature of 80° C., and separating according to hydrophobicity on a C8 column. Eluting A beta is detected by way of UV absorption at 215 nm. The peak area integration can be performed with Agilent ChemStation software. By considering the resultant values in the computation with a previously conducted calibration, it is possible to calculate the concentration of A beta present in the particular fraction. Depending on the fraction, the mean value from multiple, for example six, experiments conducted independently of one another can be calculated with the resulting standard deviation. The advantage of HPLC analysis is that detection is very sensitive (such as approximately 20 nM or 1.8 ng Aß 1-42) and quantification is reliable independently of the state of aggregation and the solvent. A decisive advantage of the method lies in the coupling of density gradient centrifugation and reverse phase HLPC, which allows also Aß oligomers to be reliably quantified.

The effect according to the invention of increased effectiveness in the elimination (or the formation) of amyloid beta species, and in particular amyloid beta oligomers, can take place with one of these methods, but not exclusively with these methods.

In a particularly preferred embodiment of the invention, the described effects of increased affinity and effectiveness of elimination, and detoxification (or formation) take place even in vitro and/or in vivo.

The cyclized peptide may comprise a linker group. The term linker group shall be understood to mean preferably additional individual amino acids in molecules, such as D3 (SEQ ID NO. 12), which may be used per se in the treatment of Alzheimer's disease so as to bind A beta constituents. The additional amino acid should not impair binding of the cyclized peptide to A beta.

Several exemplary sequences of cyclic peptides that may be used according to the invention are listed below:
cD3: rprtrlhthrnr (SEQ ID NO: 8),
cRD2: ptlhthnrrrrr (SEQ ID NO: 3) or multiples and homologs thereof.

All other linear peptides in cyclized form that effectively bind to A beta are advantageously covered according to the invention.

In a particularly advantageous embodiment of the invention, the peptide according to the invention comprises at least 2, 3, 4, 5, 6, 7, 8, 9, 10 or more peptide building blocks that separately each effectively bind to A beta, wherein these may be identical or non-identical peptide building blocks. These peptide building blocks are linearly coupled head to head, tail to tail, or head to tail, and are overall cyclized by a covalent bond, with or without additional linker building blocks (such as one or more amino acids), such as via the two ends thereof.

The at least two peptide monomer units, in turn, may be covalently or non-covalently bonded to each other, for example by way of a biotin group or a streptavidin tetramer. The peptides are characterized by units that are linearly coupled head to head, tail to tail, or head to tail.

The following shall be mentioned solely by way of example:

```
cRD2D3:
                                   (SEQ ID NO: 1)
ptlhthnrrrrrrprtrlhthrnr cD3D3:
                                   (SEQ ID NO: 2)
rprtrlhthrnrrprtrlhthrnr cRD2:
                                   (SEQ ID NO: 3)
ptlhthnrrrrr cRD2RD2,
                                   (SEQ ID NO: 4)
ptlhthnrrrrrptlhthnrrrrr cD3r,
                                   (SEQ ID NO: 5)
rprtrlhthrnrr cD3p,
                                   (SEQ ID NO: 6)
rprtrlhthrnrp cD3a,
                                   (SEQ ID NO: 7)
rprtrlhthrnra cD3:
                                   (SEQ ID NO: 8)
rprtrlhthrnr cDB3,
                                   (SEQ ID NO: 9)
rpitrlrthqnr cDB3DB3,
                                   (SEQ ID NO: 10)
rpitrlrthqnrrpitrlrthqnr cD3(p2k),
                                   (SEQ ID NO: 11)
rkrtrlhthrnr
``` or multiples and homologs thereof.

It is also possible for any arbitrary combination of 2, 3, 4, 5, 6, 7, 8, 9, 10 or more of the above-described sequences in cyclized form to form the peptide according to the invention.

Since the target molecule of the therapeutic treatment is preferably an A beta oligomer, and thus naturally a multivalent target, a particularly preferred embodiment of the invention uses the substance that, for treatment, which is to say for destruction of A beta oligomers that are present, is composed of multiple copies of an already efficient A beta oligomer-binding unit, or of multiple different already efficient A beta oligomer-binding units. These peptides are likewise cyclized. In this case, the peptide according to the invention comprises multiple peptide building blocks that, per se, effectively bind to A beta species, and in particular to A beta oligomer, each being composed of amino acids and cyclized overall by a covalent bond.

In a further variant, the peptide building blocks comprise fragments of the above-mentioned sequences or comprise homologous sequences with respect to the above-mentioned sequences.

Within the meaning of the invention, "homologous sequences" or "homologs" shall mean that an amino acid sequence has an identity of at least 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% with one of the above-mentioned amino acid sequences of the monomers. Instead of the term "identity," the terms "homologous" or "homology" are used as synonyms in the present description. The identity between two nucleic acid sequences or polypeptide sequences is calculated by comparison with the aid of the BESTFIT program, based on the algorithm by Smith, T. F. and Waterman, M. S (Adv. Appl. Math. 2: 482-489 (1981)), setting the following parameters for amino acids: Gap creation penalty: 8 and Gap extension penalty: 2; and setting the following parameters for nucleic acids: Gap creation penalty: 50 and Gap extension penalty: 3. The identity between two nucleic acid sequences or polypeptide sequences is preferably defined by the identity of the nucleic acid sequence/polypeptide sequence over the entire respective sequence length, as it is calculated by comparison with the aid of the GAP program, based on the algorithm by Needleman, S. B. and Wunsch, C D. (J. Mol. Biol. 48:

443-453), setting the following parameters for amino acids: Gap creation penalty: 8 and Gap extension penalty: 2; and setting the following parameters for nucleic acids: Gap creation penalty: 50 and Gap extension penalty: 3.

Two amino acid sequences are the same within the meaning of the present invention if they have the same amino acid sequence.

In particular, all linear peptides comprising amino acid sequences that, after cyclization, yield the same, no longer distinguishable amino acid order, are identical in this regard. Example: The linear amino acid sequence of D3 (SEQ ID NO. 12) is rprtrlhthrnr. The corresponding cyclized peptide "cD3" (SEQ ID NO. 8) linked between the N-terminal amino group and the C-terminal carboxyl group by an amide bond is no longer distinguishable from the cyclized peptides prtrlhthrnrr (SEQ ID NO. 13), rtrlhthrnrrp (SEQ ID NO. 14), trlhthrnrrpr (SEQ ID NO. 15), rlhthrnrrprt (SEQ ID NO. 11), lhthrnrrprtr (SEQ ID NO. 17), hthrnrrprtrl (SEQ ID NO. 18), thrnrrprtrlh (SEQ ID NO. 19), hrnrrprtrlht (SEQ ID NO. 20), rnrrprtrlhth (SEQ ID NO. 21), nrrprtrlhthr (SEQ ID NO. 22), or rrprtrlhthrn (SEQ ID NO. 23). The positive effects of the cyclized peptides according to the invention in terms of affinity and effectiveness moreover occur with respect to at least one, and preferably with respect to each linear binding peptide from which it can be derived. In the case of cyclized D3 (SEQ ID NO. 8), this means with respect to linear binding peptides having the sequence prtrlhthrnrr (SEQ ID NO. 13), rtrlhthrnrrp (SEQ ID NO. 14), trlhthrnrrpr (SEQ ID NO. 15), rlhthrnrrprt (SEQ ID NO. 16), lhthrnrrprtr (SEQ ID NO. 17), hthrnrrprtrl (SEQ ID NO. 18), thrnrrprtrlh (SEQ ID NO. 19), hrnrrprtrlht (SEQ ID NO. 20), rnrrprtrlhth (SEQ ID NO. 21), nrrprtrlhthr (SEQ ID NO. 22), or rrprtrlhthrn (SEQ ID NO. 23). Cyclized peptides according to the invention in this connection exhibit a) higher binding affinity to amyloid beta species than at least one, preferably each, of the linear peptides from which it can be derived. Cyclized peptides according to the invention exhibit b) a higher effectiveness in the prevention of the formation and/or in the detoxification, in particular of amyloid beta oligomers, than at least one, preferably each, of the linear, binding peptides from which the cyclized peptide can be derived. The above-mentioned cyclized D3 (SEQ ID NO. 8) shall be understood to be mentioned solely by way of example. The effects thus occur in particular, but not exclusively, with the cyclized peptides of SEQ ID NO. 1-11.

In one variant, homologs shall be understood to mean the corresponding retro-inverse sequences of the above-mentioned building blocks. According to the invention, the term "retro-inverse sequence" denotes an amino acid sequence that is composed of amino acids in the enantiomeric form (inverse: chirality of the alpha carbon atom is inverted), and in which additionally the sequence order was reversed compared to the original amino acid sequence (retro=reverse).

The peptide building blocks and peptide polymers according to the invention, or generally speaking the peptides according to the invention, are suitable for use in medicine.

In one embodiment, these are peptides according to the invention for treating Alzheimer's disease. In a further embodiment, these are peptides according to the invention that can be used to treat Parkinson's, Creutzfeldt-Jakob Disease (CJD), amyotrophic lateral sclerosis (ALS), or other neurodegenerative diseases, or diabetes.

The present invention further relates to a kit containing the peptide according to the invention. In such a kit, the peptides according to the invention can be packaged in containers, optionally with/in buffers or solutions. All components of the kit may be packaged in the same container or separately from each other. The kit can moreover include instructions for the use thereof. Such a kit can include, for example, the peptides according to the invention in an injection vial having a stopper and/or septum. A disposable syringe can also be included therein, for example.

The present invention also relates to the use of the peptides according to the invention as a probe for identifying and qualitatively and/or quantitatively determining in particular amyloid beta oligomers. The present invention further relates to the probe itself, including the peptide according to the invention for identifying and qualitatively and/or quantitatively determining amyloid beta oligomers, in particular.

Such probes are of great importance in enabling early diagnosis of Alzheimer's disease. This allows the disease to be counteracted at a very early stage. Moreover, the progression of the disease or progress of a treatment attempt or of a treatment can be tracked in this way.

Such molecular probes contain the peptide according to the invention and can be injected in the patient, for example intravenously. Further components of the probe may be: dyes, fluorescent dyes, radioactive isotopes (for example for PET), gadolinium (for MRI), and/or components that are used for probes in imaging. Prior to or after passing the blood-brain barrier, the probes can bind in particular to A beta oligomers and/or plaque. The amyloid beta species thus marked, and in particular the A beta oligomers and/or plaque thus marked, can be rendered visible using imaging processes, such as SPECT, PET, CT, MRI, near infrared (NIR), proton MR spectroscopy and the like.

The present invention moreover relates to the use of the cyclized peptide for the prevention of the multiplication and/or the formation, and/or detoxification of toxic amyloid beta oligomers. The peptides according to the invention are thus also used to form non-toxic peptide-amyloid beta oligomer complexes.

The present invention also relates to a composition containing the peptide according to the invention, in particular for treating or preventing Alzheimer's disease.

The present invention further relates to a composition containing the peptide according to the invention, in particular for preventing toxic A beta oligomers, or for destroying polymers or fibrils formed thereof.

The "composition" according to the invention can be a vaccine, a drug (such as in tablet form), an injection solution, a food or dietary supplement, for example, containing the peptide according to the invention in a formulation to be produced based on expert knowledge.

The peptides according to the invention detoxify the A beta oligomers or aggregates and fibrils formed thereof by binding thereto, thus converting them into non-toxic compounds. Substances that are able to inhibit the formation of fibrils do not necessarily also have to be able to destroy preformed fibrils, since preformed A beta fibrils are very stable and are very difficult and slow to destroy again.

The present invention thus also relates to a method for detoxifying the A beta oligomers, or polymers or fibrils formed thereof.

It was found that, when Aß oligomers are already present, the goal of a treatment must be to address these with substances that have the highest possible affinity to A beta. De facto, the affinity cannot be high enough, and the corresponding dissociation constant of the peptide according to the invention is then in the pM range or even lower.

It was furthermore found that an important difference between prevention and treatment lies in the following consideration. So as to prevent the formation of initial A beta oligomers, A beta ligands having low affinity and effectiveness may already suffice. Since the formation of an A beta oligomer from multiple A beta monomers is a reaction of a very high order, it is dependent to a high degree on the A beta monomer concentration. Even a small reduction in the active A beta monomer concentration can thus prevent the initial A beta oligomers from forming. This is the situation with prevention.

However, if A beta oligomers have already been created, these are able to multiply (in a prion-like manner), which is not a reaction of a high order and consequently almost no longer dependent on the A beta monomer concentration. This is the situation with treatment. If A beta oligomers have already been created, the goal of a treatment must be to address these with substances that have the highest possible affinity to Aß oligomers and/or to eliminate these particularly efficiently and/or to prevent formation particularly efficiently. The corresponding dissociation constant would have to be in the sub-µM, nM or pM range, or even lower. This is the case in the present invention, and the cyclized peptides according to the invention, in the spirit of the treatment, bind the amyloid beta species, and in particular the A beta oligomers, with an accordingly low dissociation constant.

As a result of the property to bind both small, freely diffusable A beta oligomers, and larger A beta oligomers and even fibrils, the peptides according to the invention can be used in all stages of Alzheimer's disease. Based on the teaching of the present invention, it is possible to produce peptides that also selectively bind to various forms of the A beta oligomers.

In addition to the above-mentioned methods for producing the peptides according to the invention, peptide synthesis methods, the recombinant production of proteins and recognized organic synthesis methods for arbitrary so-called low molecular weight compounds are possible choices, for example.

In particular, covalent cyclization of this linear molecule is conceivable. This avoids in particular one, and advantageously even two, open ends of the peptide chain. This increases the stability of the peptide in animals and humans, resulting in considerably more advantageous pharmacokinetic properties. The cyclization, however, particularly advantageously also causes the number of possible conformations of the peptide in the unbound state to be drastically reduced. This, in turn, reduces the entropy in the free state, which makes the entropic part of the binding reaction again more advantageous for the benefit of forming a complex with the target molecule A beta. Ultimately, this considerably increases the affinity to the target molecule compared to the linear, binding peptide from which the cyclized peptide can be derived. The same applies to the effectiveness of the elimination and/or prevention of the formation of toxic amyloid beta species, and in particular of the amyloid beta oligomers. These effects according to the invention are crucial in this process, rather than potentially increased stability, which is only a positive side-effect of cyclization.

This cyclization takes place, for example, by head-to tail or tail-to-head or other cyclizations of the linear peptide. Any possible cyclization may be considered for this purpose.

Since the target molecule of the therapeutic treatment is in particular an A beta oligomer, and thus naturally a multivalent target, the idea is to produce the substance to be used for treatment (destruction of existing A beta oligomers) from multiple copies of an already efficiently A beta oligomer-binding peptide unit, which are advantageously additionally cyclized. In this case, the peptide comprises multiple peptide building blocks which per se already effectively bind to A beta oligomer and which each have a linear composition of amino acids, and which, in the overall, are joined between the remaining two ends to form a cycle.

This measure advantageously achieves a further reduction of the KD. It is thus advantageously achieved that, at least theoretically and in the absence of interfering influences, such as through steric hindrance, an n-mer of an A beta oligomer-binding unit that binds to A beta oligomers with a dissociation constant (KD) of x achieves an apparent KD of x to the power of n.

A wide variety of options exist to achieve this. The A beta oligomer-binding units, which is to say the peptide monomer units, can be covalently or non-covalently bonded to each other, for example by way of a biotin group or a streptavidin tetramer.

A covalent bond can be achieved by linearly coupling the monomer units head to head, tail to tail, or head to tail, and more particularly without a linker group or with a linker group. It is also possible to combine non-identical monomer units and cyclize these according to the invention.

The invention will be explained in more detail hereafter with reference to exemplary embodiments and the attached figures. The invention is not limited thereby in any way. Rather, it will be clear to a person skilled in the art that they may, within the scope of their knowledge in the art, produce other peptides, which are proven to effectively bind to A beta species, in cyclized form and use these to prevent and treat Alzheimer's disease.

DESCRIPTION OF THE PREFERRED EMBODIMENTS

Figure 1:
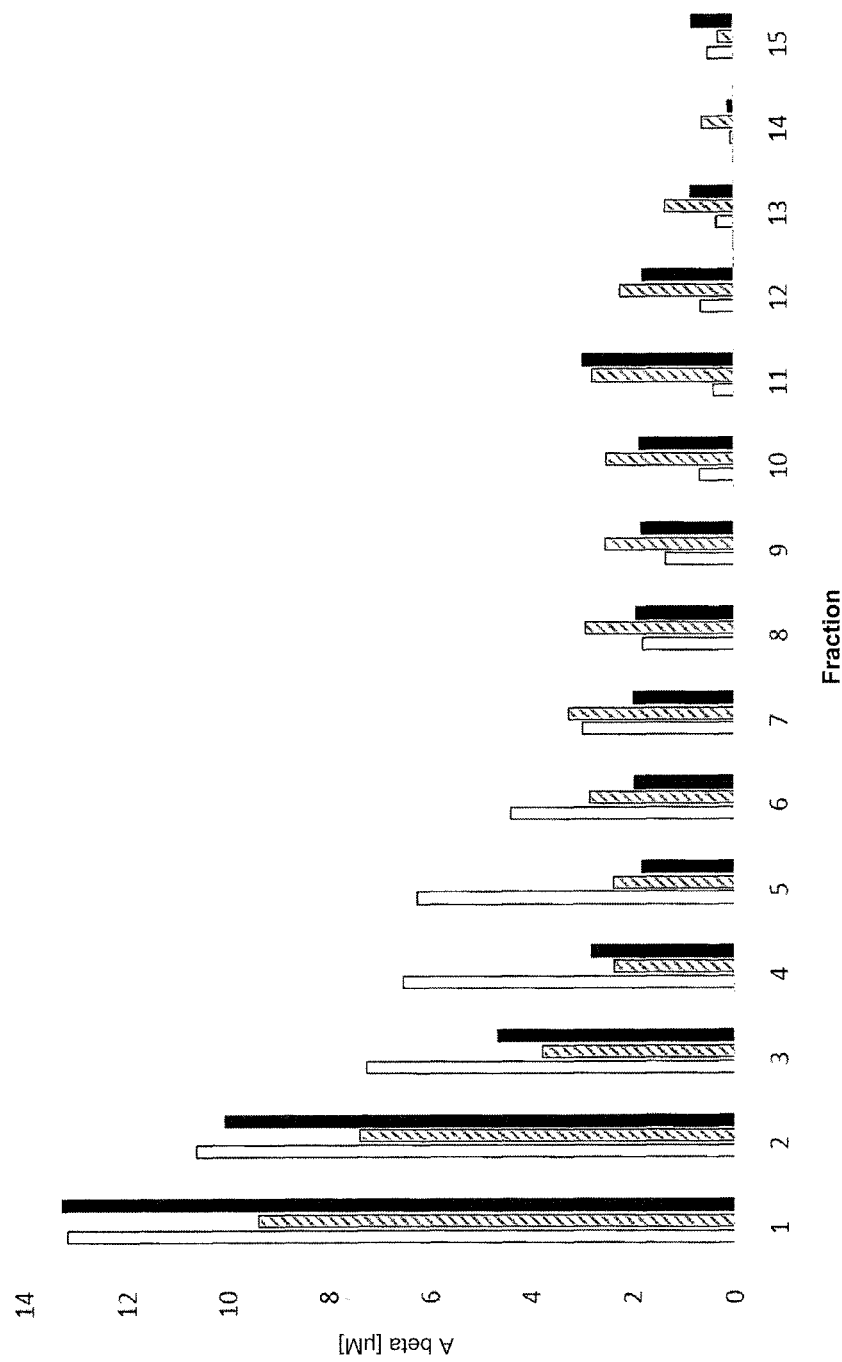
FIG. 1 shows the change of the fractions of a standardized density gradient centrifugation after adding linear D3 (SEQ ID NO. 12) (prior art) and cD3 (cyclized D3) (SEQ ID NO. 8). The comparison of the influence of D3 (SEQ ID NO. 12) (hatched bars) and cD3 (black) (SEQ ID NO. 8) on the size distribution of the A beta aggregates (control in white) shows that cD3 (SEQ ID NO. 8) eliminates the oligomers in fractions 4 to 8 even more efficiently than linear D3 (SEQ ID NO. 12).

The D-enantiomeric linear peptide by the name D3 (SEQ ID NO. 12) is known from the publication WO 02081505 A2. It was identified by way of a mirror image phage display selection against predominantly monomeric A beta (1-42), with the goal of stabilizing the same with the bond and preventing conversion into toxic A beta aggregates. Based on current knowledge, D3 (SEQ ID NO. 12) preferably binds the particularly toxic A beta oligomers, precipitates these, and converts them into non-toxic, non-amyloidogenic and ThT negative amorphous aggregates. In animal models, even oral administration of D3 (SEQ ID NO. 12) with drinking water results in treated transgenic AD mice containing considerably less plaque and having significantly improved cognitive abilities.

First Exemplary Embodiment

The first exemplary embodiment is intended to show the increase in effectiveness or efficiency of D3 (SEQ ID NO. 12) in the decomposition of the amyloid beta oligomers by way of cyclization. For this purpose, the N-termini and the C-termini of the first and last amino acids of the linear binding peptide D3 (SEQ ID NO. 12) were covalently bound by way of a peptide bond.

Cyclized D3 ("cD3") (SEQ ID NO. 8) according to the invention was obtained from peptides&elephants GmbH (Am Mühlenberg 11, 14476 Potsdam-Golm, Germany).

The following method was employed to produce the fractions from the density gradient centrifugation. The conformers were separated according to the s value or sedimentation coefficient thereof. Molecules of differing sizes can have an identical hydrodynamic radius, but nonetheless have different s values and are separated according to these. Calibration using molecules having a known s value allows the A beta conformers obtained by way of density gradient centrifugation to be exactly determined according to the s value thereof. Density gradient centrifugation has the advantage that this allows all A beta conformers to be separated from each other in a single method step. By using the density gradient centrifugation step prior to immobilization, in which oligomers or higher A beta forms are layered onto a preformed density gradient and the aggregate particles contained therein are separated according to the s value thereof by way of ultracentrifugation, it is possible, over the course of the centrifugation, to separate different A beta aggregates (oligomers and fibrils or amorphous aggregates) from each other according to the sedimentation coefficient thereof, which depends on the particle size, among other things, and fractionate these. The fraction containing the desired A beta conformer can then be directly injected onto a streptavidin-loaded sensor surface for immobilization. The density gradient was prepared by subsequently layering thereon the density gradient solution (iodixanol diluted in 10 mM sodium phosphate buffer pH 7.4) in concentrations of 50% (260 µl), 40% (260 µl), 30% (260 µl), 20% (260 µl), 10% (260 µl), and 5% (100 µl) (v/v). Thereafter, the samples were pipetted onto the density gradient and centrifugation was carried out for 3 hours at 4° C. and 259000 g. A total of 14 fractions at 140 µl each were then removed from the density gradient from top to bottom. Monomers can be found in the first fractions, oligomers in particular starting with fractions 4, and fibrils are typically present in fractions 11 to 13.

The fractions obtained from the density gradient centrifugation were either untreated (control: respective left, blank column) or treated with the D3 (SEQ ID NO. 12) known from the prior art (D3: 20 µM: respective center, hatched column) or else treated with the cyclized variant (SEQ ID NO. 8) of the molecule D3 (SEQ ID NO. 12), in which the N-termini and the C-termini of the first and last amino acids were covalently bound by way of a peptide bond (cD3, 20 respective right, black column).

The result is shown in FIG. 1. It is apparent that the cyclized cD3 (SEQ ID NO. 8) advantageously shows no influence on the A beta monomer concentration of fractions 1 to 2.

With respect to fractions 4 to 8, or 4 to 10, however, advantageously a clear decrease in the A beta oligomer concentration is apparent.

A comparable effect also occurs with the remaining peptides according to the invention.

Second Exemplary Embodiment

The following steps refer both to affinity studies and to studies on the decomposition of particularly toxic amyloid beta oligomers.

Production of Aß Monomers, Oligomers, and Fibrils 1 mg lyophilized Aß1-42 and N-terminal biotinylated Aß1-42 were each dissolved in 1 ml 100% hexafluoroisopropanol (HFIP) and dissolved overnight at room temperature. For the oligomer and fibril preparation, non-biotinylated Aß was used with N-terminal biotinylated Aß at a ratio of 1:10 and the HFIP was evaporated (Concentrator 5301 from Eppendorf). The resultant Aß film, at a final concentration of 80 µM, was placed in sodium phosphate buffer (10 mM, pH 7.4) and incubated (RT, 600 rpm). The incubation time was 3 h for the oligomer preparation, and 24 h for the fibril preparation. 100% N-terminal biotinylated Aß1-42 without incubation was used for the preparation of monomers.

Density Gradient Centrifugation

The density gradient centrifugation was carried out subsequent to the Aß preparation to purify the respective Aß species according to the size of the same. An iodixanol gradient in 10 mM sodium phosphate buffer, pH 7.4 with rising concentrations from 50% to 5% v/v iodixanol was used for this purpose. 100 µl of the Aß sample was applied and separated by way of ultracentrifugation (3 h, 4° C., 259000 g). Subsequently, the gradient was fractionated into 14 fractions, 140 µl each. Monomeric Aß are present in the first two top fractions, Aß oligomers in fractions 4 to 6, and Aß fibrils in fractions 11 to 13.

Immobilization for Surface Plasmon Resonance (SPR) Spectroscopy

A T200 from Biacore (GE Healthcare) was used for SPR spectroscopy. The Aß species purified by way of density gradient centrifugation were directly immobilized on a sensor chip (Series S Sensor Chips SA) according to the manufacturer's instructions by way of biotin-streptavidin coupling. 1×PBS was used as the running buffer. Loading took place at 25° C. and a flow rate of 5 µl/min. Subsequently, the flow cells were freed from non-specifically bound ligand overnight at a steady flow of 30 µl/min.

Binding Kinetics

Binding kinetics were likewise measured by way of SPR spectroscopy using a T200 device from Biacore (GE Healthcare). The standard conditions are 25° C. and a flow rate of 30 µl/min. Different lyophilizates of the D peptides were placed in the 1×PBS running buffer and serially diluted. The method used was a "single-cycle" kinetics method, wherein five increasing analyte concentrations were pumped over the immobilized flow cells. The contact times selected, depending on the analyte, were 90 to 120 s for association and dissociation and 1800 to 5400 s for the final dissociation. The sensorgrams were double referenced with the aid of an unloaded flow cell and the running buffer that was used. The binding curves were evaluated by way of kinetic fit models (heterogeneous binding model) using the Biacore T200 evaluation software (version 2.0).

Figure 2:
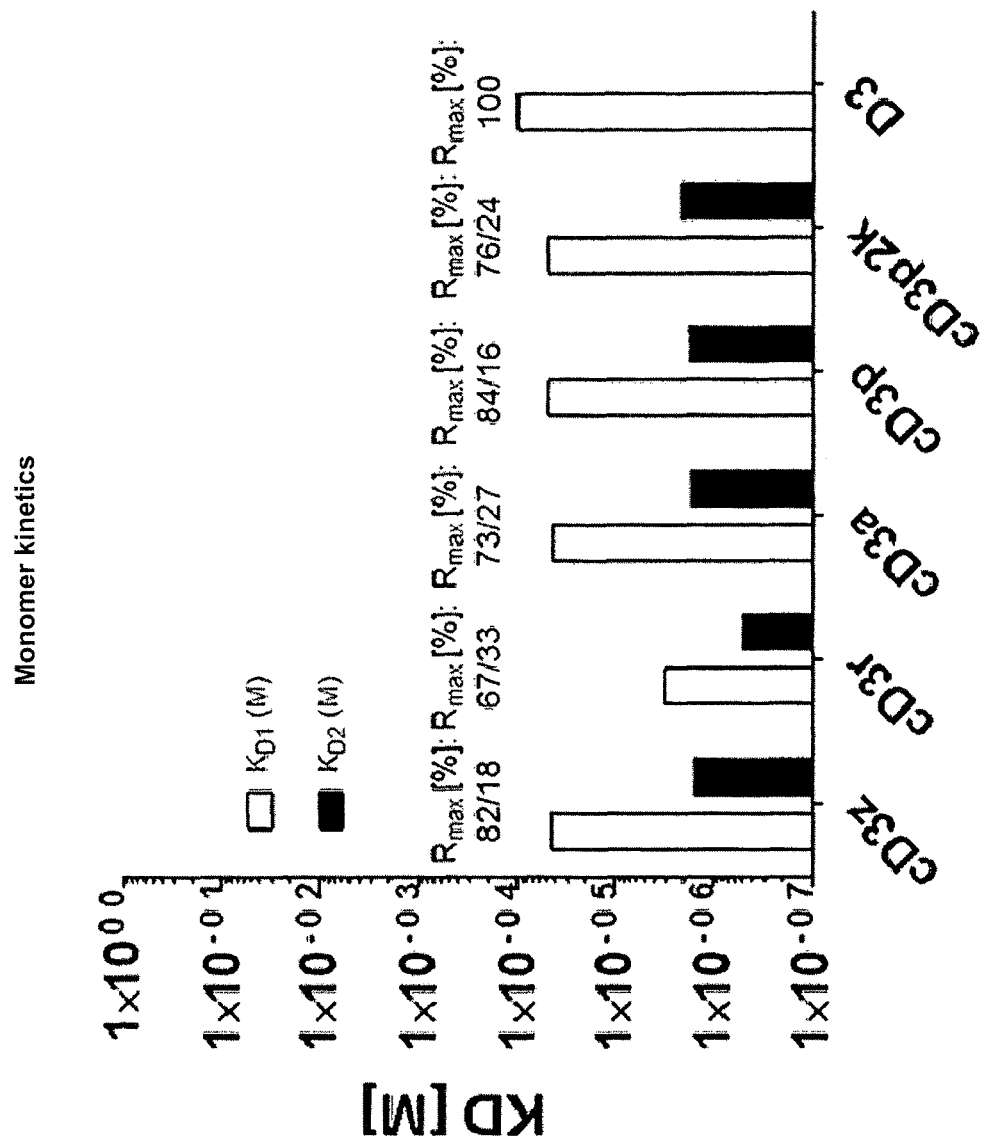
FIG. 2 shows $K_D$ values (kinetics) for amyloid beta monomer.
Figure 3:
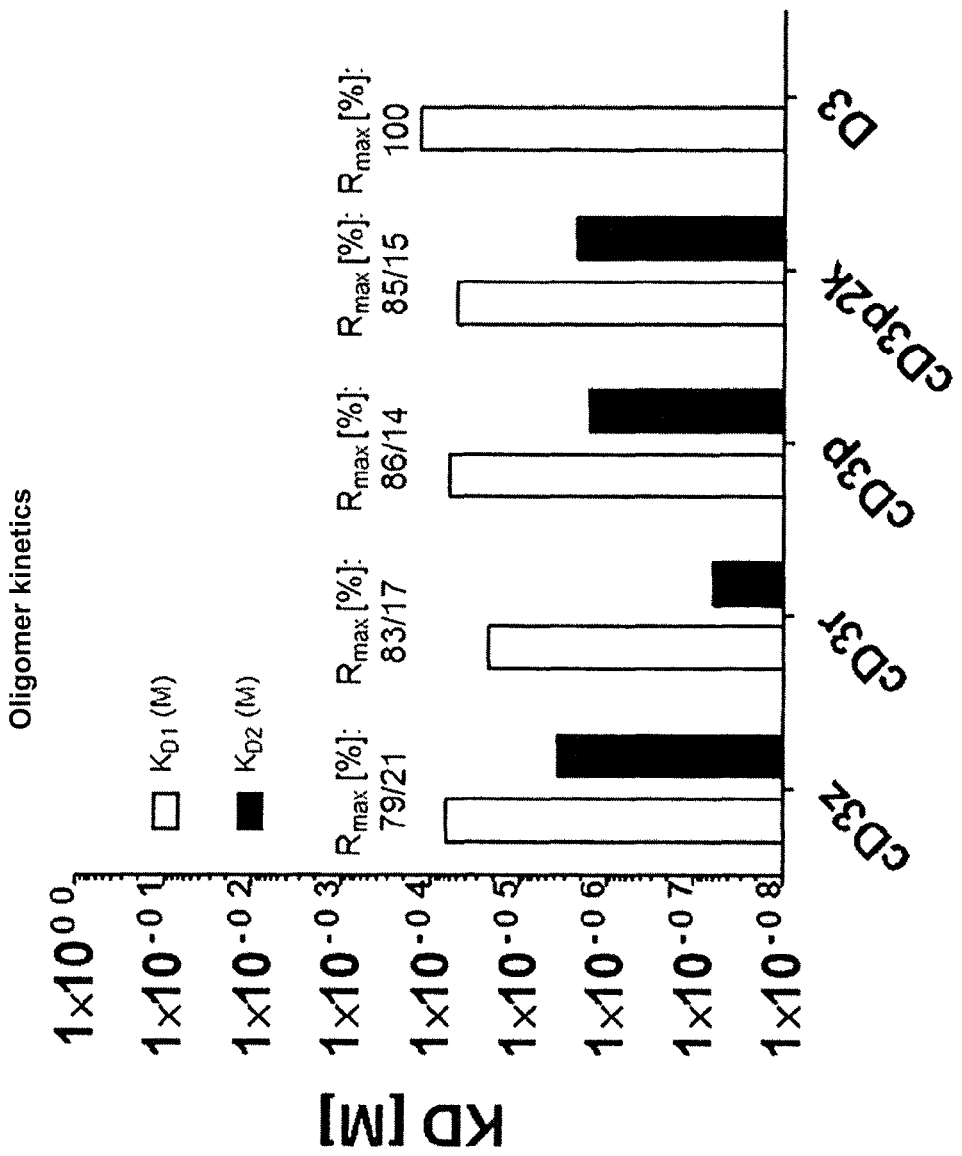
FIG. 3 shows $K_D$ values (kinetics) for amyloid beta oligomer.
Figure 4:
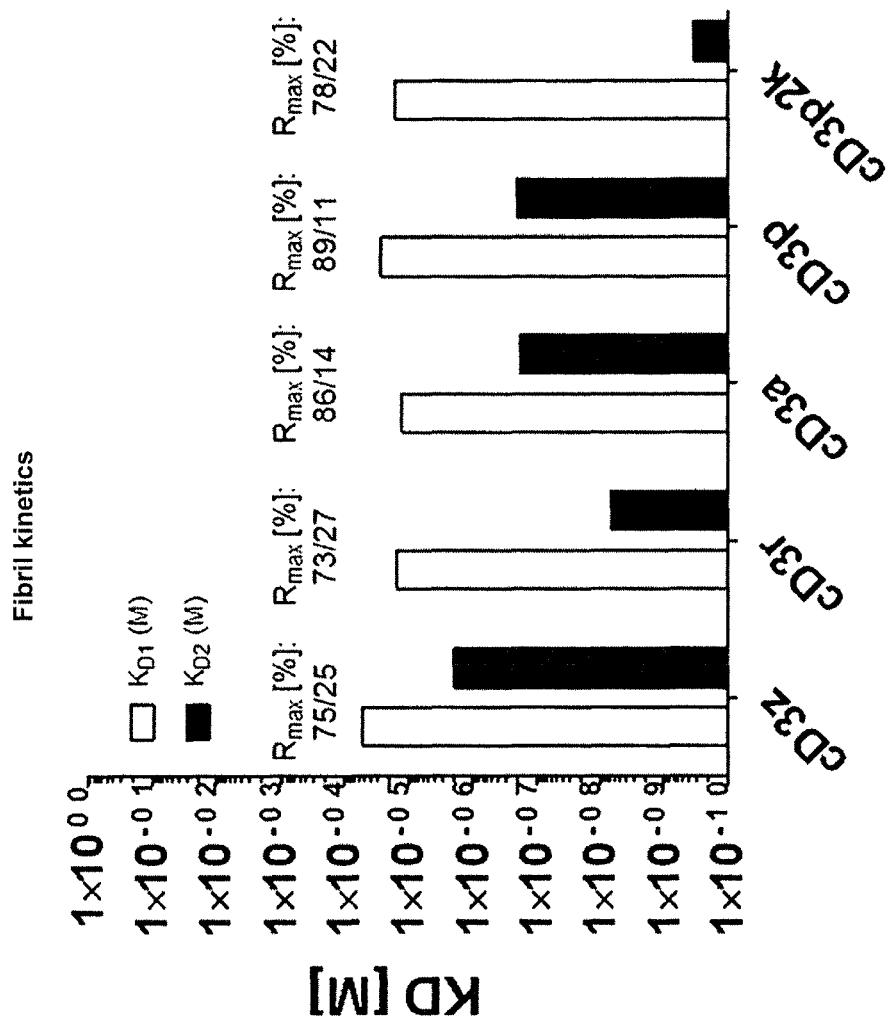
FIG. 4 shows $K_D$ values (kinetics) for amyloid beta fibrils.

FIGS. 2 to 4 show the results on the binding behavior of the cyclized peptides according to the invention (affinity study). The figures show data for the kinetic evaluation of the binding strength of the various candidates to amyloid beta monomers (FIG. 2), amyloid beta oligomers (FIG. 3), and amyloid beta fibrils (FIG. 4). The two binding constants that result when fitting a heterogeneous binding model are shown in each case, plotted as white bars and black bars. It is important to remember that a logarithmic scale is shown here, which means that minor differences in the bar size represent major differences in the dissociation constant $K_D$. White bars are the respective low-affinity sites and the binding strengths thereof, and black bars show the high-affinity binding sites and the binding strengths thereof.

It is shown that a homogeneous 1:1 binding model is only sufficient for fitting the binding curves in the case of the linear peptide D3 (SEQ ID NO. 12).

It is also shown that the white bars for the low-affinity binding sites are similarly high in almost all instances of the cyclized peptides that are used. However, big differences result in the high-affinity binding sites, which are shown as black bars.

It also becomes apparent that the cyclic cD3r (SEQ ID NO. 5) does very well among the monomers (FIG. 2), which is to say has particularly high affinity.

Among the oligomers that are of particular interest, cD3r (SEQ ID NO. 5) binds even more strongly by two orders of magnitude than the other cyclized peptides according to the invention (FIG. 3).

The cD3r (SEQ ID NO. 5) also does very well among the fibrils compared to the other peptides according to the invention, wherein here, as a peculiarity, the peptide according to the invention cD3P2K (SEQ ID NO. 11) does extremely well and advances as far as the sub-pM binding range (FIG. 4).

The Rmax values in FIGS. 2 to 4 indicate how strong the contribution of the respective KD to the overall loading capacity is. In the example of the oligomers (FIG. 3), an Rmax of 79/21% is shown for the peptide cD3z. cD3z denotes cD3 zero, which is to say cyclized D3 (SEQ ID NO. 8) without any further amino acid attachments. The white bar indicates that the low-affinity site can yield a total of 79% of the RU total loading strength and KD2 a total of 21% of the RU. This means that a ratio of approximately 1:4 exists for this peptide at binding sites, which is to say there are approximately 4 times as many low-affinity sites as high-affinity sites.

The observation that no high-affinity site is yielded for the linear peptide D3 (SEQ ID NO. 12) when fitting the experimental binding data can be explained by the fact that it either does not bind to the high-affinity site, or that the affinities to the high-affinity site and low-affinity site cannot be distinguished.

It becomes apparent from this data that the linear D3 (SEQ ID NO. 12) binds only a low-affinity site, but not a high-affinity site in the case of amyloid beta oligomer.

Figure 5:
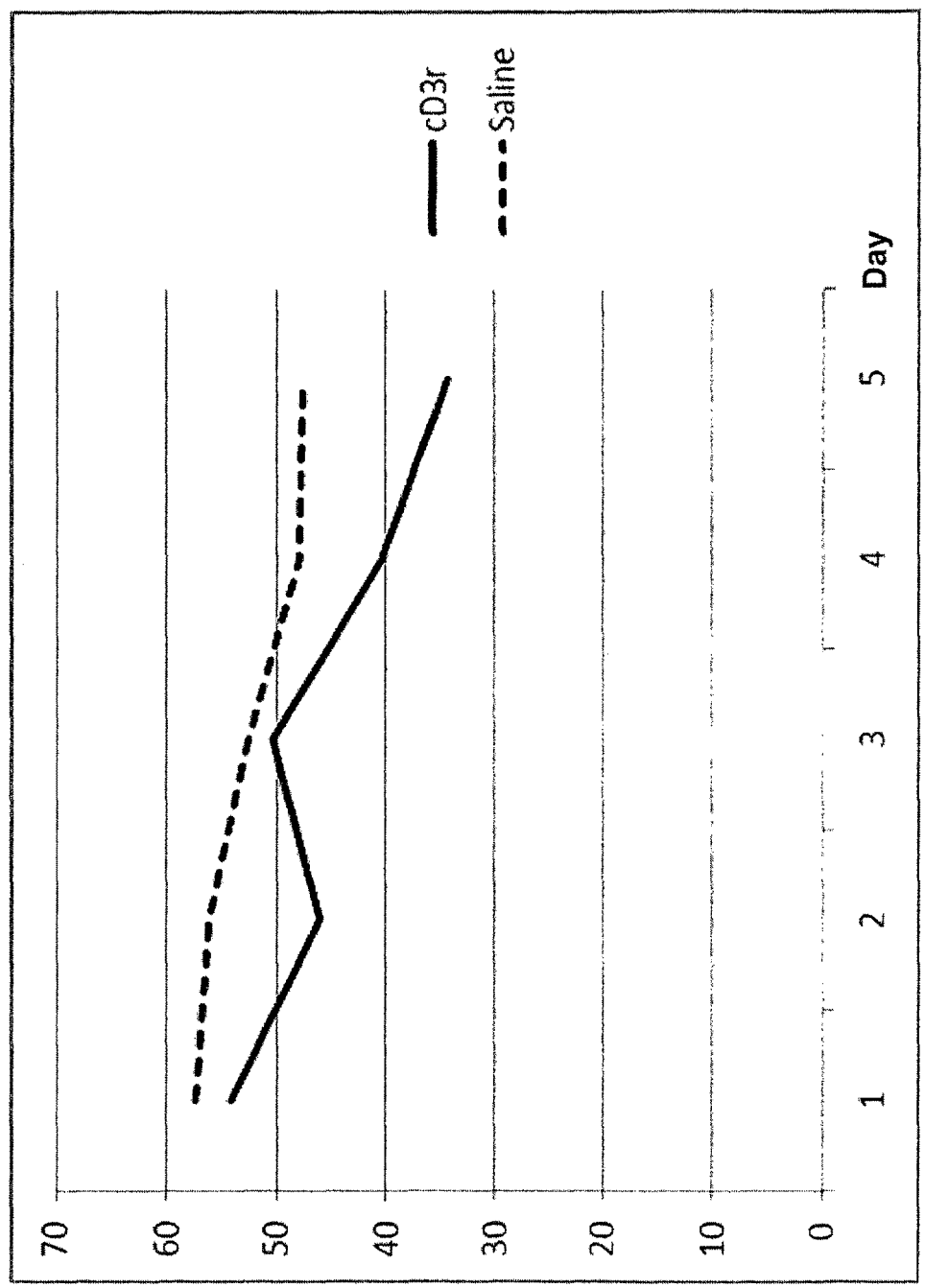
FIG. 5 shows the Morris water maze (MWW) test.

FIG. 5 shows in vivo data from the MWW test. The test measures the spatial memory of animals, which here were genetically engineered APPsDI mice. These mice exhibit behavioral abnormalities and biochemical changes that characterize one aspect of Alzheimer's disease, namely a memory disorder.

The time is measured in seconds that an animal requires to locate a platform hidden closely beneath the water surface in a water tank. This is measured in several experiments per day on several consecutive days. A statistical evaluation then shows whether the learning in terms of locating the platform was better among the treated animals compared to the control group. The search time is plotted in seconds on five consecutive days for mice that were treated with the peptide according to the invention cD3R (SEQ ID NO. 5), compared to placebo experiments (saline).

The learning of animals treated with the cyclized peptide cD3r (SEQ ID NO. 5) was significant (non-parametric Friedmann test, asymptotic significance cD3r=0.014; asymptotic significance saline=0.238).

The sequence listings for SEQ ID NO 1 through SEQ ID NO. 23 as found in the 5 kb text file named "SequenceListing03.txt" created and uploaded to EFS-Web on Apr. 17, 2018 are incorporated herein by reference.

The sequence listings for SEQ ID NO. 1 and SEQ ID NO. 11, as found in the 3 kb text file named 'F11599SequenceListing01 .txt' created and uploaded to EFS-Web on May 4, 2017 are incorporated herein by reference.

The invention claimed is:

1. A cyclic peptide comprising:
a linear sequence of amino acids from a first amino acid to a last amino acid for binding to amyloid beta species, wherein the linear sequence comprises one or more sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10 and SEQ ID NO: 11;
wherein said linear sequence of amino acids is in a cyclic form in which a first amino acid of the linear sequence has a covalent bond to a last amino acid of the linear sequence either directly or via a linker group comprising biotin or a streptavidin tetramer.

2. The cyclic peptide according to claim 1, which is substantially composed of D-enantiomeric amino acids.

3. The cyclic peptide according to claim 1, bound to amyloid beta species at a plurality of binding sites on the cyclic peptide with a dissociation constant (KD value) of no more than 1 μM.

4. The cyclic peptide according to claim 1, wherein the cyclic peptide comprises the linker group,
wherein said linker group is not part of said linear sequence, and
wherein said linear sequence of amino acids has said cyclic form in which said first amino acid has said covalent bond to said last amino acid via said linker group.

5. The cyclic peptide according to claim 1, bound to said amyloid beta species, wherein said linear sequence of amino acids comprises a plurality of the sequences selected from the group consisting of SEQ ID NO: 1 SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10 and SEQ ID NO: 11 each one of said plurality of sequences being bound to said amyloid beta species and said linear sequence remaining in said cyclic form with said covalent bond while bound to said amyloid beta species.

6. The cyclic peptide according to claim 1, wherein said linear sequence consists of a plurality of identical sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10 and SEQ ID NO: 11 bonded to each other.

7. The cyclic peptide according to claim 1, wherein said linear sequence consists of a plurality of sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10 and SEQ ID NO: 11 covalently bonded to each other.

8. The cyclic peptide according to claim 1, wherein said linear sequence of amino acids comprises a plurality of sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10 and SEQ ID NO: 11.

9. A kit, comprising at least one cyclic peptide according to claim 1 and a container in which the at least one cyclic peptide is packaged.

10. A probe, comprising at least one cyclic peptide according to claim 1 and a material selected from the group consisting of dyes, fluorescent dyes, radioactive isotopes and gadolinium.

11. A method for treating Alzheimer's disease, comprising administering to a person suffering from Alzheimer's disease a composition comprising at least one cyclic peptide according to claim 1.

12. A method for identifying and quantitatively and/or qualitatively determining amyloid beta species, comprising contacting amyloid beta species with a probe comprising the cyclic peptide of claim 1.

13. A method for reducing formation of amyloid beta oligomers from amyloid beta species, comprising contacting the amyloid beta species with the cyclic peptide of claim 1.

14. A method for forming non-toxic polymer-amyloid beta oligomer complexes from amyloid beta species, comprising contacting the amyloid beta species with the cyclic peptide of claim 1.

15. The cyclic peptide according to claim 1 bound to said beta amyloid species at a first plurality of high-affinity binding sites on the cyclic peptide and bound to said beta amyloid species at a second plurality of low-affinity binding sites on the cyclic peptide,
wherein each high affinity binding site among said first plurality has a dissociation constant (KD value) of no more than 1 µM.

16. The cyclic peptide according to claim 1, bound to amyloid beta oligomers at a plurality of binding sites on the cyclic peptide with a dissociation constant (KD value) of no more than 100 nM.

17. The cyclic peptide according to claim 1, bound to amyloid beta fibrils at a plurality of binding sites on the cyclic peptide with a dissociation constant (KD value) of no more than 10 nM.

18. A cyclic peptide comprising:
a linear sequence of amino acids from a first amino acid to a last amino acid for binding to amyloid beta species, wherein the linear sequence comprises one or more sequences selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10 and SEQ ID NO: 11; and
wherein said linear sequence of amino acids is in a cyclic form in which a first amino acid of the linear sequence has a covalent bond directly to a last amino acid of the linear sequence.

* * * * *